US012667561B2

(12) United States Patent
Magaña Castro et al.

(10) Patent No.: US 12,667,561 B2
(45) **Date of Patent: *Jun. 30, 2026**

(54) GEL CONTAINING PIRFENIDONE

(71) Applicant: Excalibur Pharmaceuticals, Inc., New York, NY (US)

(72) Inventors: José Agustín Rogelio Magaña Castro, Mexico City (MX); Laura Vázquez Cervantes, Mexico City (MX); Juan Socorro Armendáriz Borunda, Mexico City (MX)

(73) Assignee: Excalibur Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/458,390

(22) Filed: Aug. 30, 2023

(65) Prior Publication Data

US 2024/0238262 A1 Jul. 18, 2024

Related U.S. Application Data

(60) Continuation of application No. 17/390,368, filed on Jul. 30, 2021, now Pat. No. 11,779,574, which is a continuation of application No. 16/450,150, filed on Jun. 24, 2019, now Pat. No. 11,083,719, which is a division of application No. 15/435,494, filed on Feb. 17, 2017, now Pat. No. 10,376,500, which is a division of application No. 13/893,626, filed on May 14, 2013, now abandoned, which is a division of application No. 12/673,304, filed as application No. PCT/MX2008/000107 on Aug. 14, 2008, now Pat. No. 8,492,412.

(30) Foreign Application Priority Data

Aug. 14, 2007 (MX) .................... MX/a/2007/009796

(51) Int. Cl.

| | |
|---|---|
| ***A61K 31/4418*** | (2006.01) |
| ***A61K 9/00*** | (2006.01) |
| ***A61K 9/06*** | (2006.01) |
| ***A61K 47/02*** | (2006.01) |
| ***A61K 47/18*** | (2017.01) |
| ***A61K 47/22*** | (2006.01) |
| ***A61K 47/32*** | (2006.01) |

(52) U.S. Cl.

CPC ........ *A61K 31/4418* (2013.01); *A61K 9/0014* (2013.01); *A61K 9/06* (2013.01); *A61K 47/02* (2013.01); *A61K 47/18* (2013.01); *A61K 47/22* (2013.01); *A61K 47/32* (2013.01)

(58) Field of Classification Search

CPC .... A61K 31/4418; A61K 47/18; A61K 47/22; A61K 9/0014; A61K 9/06

See application file for complete search history.

(56) References Cited

U.S. PATENT DOCUMENTS

| | | | |
|---|---|---|---|
| 4,105,782 | A | 8/1978 | Yu et al. |
| 4,256,877 | A | 3/1981 | Karlsson et al. |
| 4,376,118 | A | 3/1983 | Daher et al. |
| 5,009,895 | A | 4/1991 | Lui |
| 5,310,562 | A | 5/1994 | Margolin |
| 5,811,130 | A | 9/1998 | Boettner et al. |
| 5,958,420 | A | 9/1999 | Jenson |
| 6,365,131 | B1 | 4/2002 | Doshi et al. |
| 7,109,246 | B1 | 9/2006 | Hawtin |
| 7,816,383 | B1 | 10/2010 | Bradford et al. |
| 8,492,412 | B2 | 7/2013 | Magana Castro et al. |
| 8,603,965 | B2 | 12/2013 | Zhou et al. |
| 9,408,836 | B2 | 8/2016 | Armendariz Borunda et al. |
| 9,949,959 | B2 | 4/2018 | Armendariz Borunda et al. |
| 9,962,374 | B2 | 5/2018 | Armendariz Borunda et al. |
| 10,376,500 | B2 | 8/2019 | Magana Castro et al. |
| 10,383,862 | B2 | 8/2019 | Armendariz Borunda et al. |
| 10,792,258 | B2 | 10/2020 | Magana Castro et al. |
| 11,013,727 | B2 | 5/2021 | Armendariz Borunda et al. |
| 11,040,030 | B2 | 6/2021 | Armendariz Borunda et al. |
| 11,052,074 | B2 | 7/2021 | Armendariz Borunda et al. |
| 11,083,719 | B2 | 8/2021 | Magana Castro et al. |
| 11,576,905 | B2 | 2/2023 | Magaña Castro et al. |
| 11,766,426 | B2 | 9/2023 | Armendáriz Borunda et al. |
| 11,779,574 | B2 | 10/2023 | Magaña Castro et al. |
| 12,083,085 | B2 | 9/2024 | Magana Castro et al. |
| 12,083,106 | B2 | 9/2024 | Armendariz Borunda et al. |
| 2003/0103941 | A1 | 6/2003 | Crombleholme et al. |
| 2003/0185872 | A1 | 10/2003 | Kochinke et al. |
| 2004/0029946 | A1 | 2/2004 | Arora et al. |
| 2004/0235946 | A1 | 11/2004 | Ott |

(Continued)

FOREIGN PATENT DOCUMENTS

| | | | |
|---|---|---|---|
| CA | 2764043 | A1 | 12/2010 |
| CN | 1701793 | A | 11/2005 |

(Continued)

OTHER PUBLICATIONS

International Search Report and Written Opinion, dated Nov. 22, 2012 for Application No. PCT/MX2012/000067.
International Preliminary Report on Patentability, dated Aug. 7, 2013 for Application No. PCT/MX2012/000067.
International Search Report and Written Opinion, dated Dec. 9, 2008 for Application No. PCT/MX2008/000107.
International Preliminary Report on Patentability, dated Dec. 1, 2009 for Application No. PCT/MX2008/000107.
International Search Report and Written Opinion, dated Apr. 9, 2018 for Application No. PCT/MX2017/000129.

(Continued)

*Primary Examiner* — San Ming R Hui

(74) *Attorney, Agent, or Firm* — Wolf, Greenfield & Sacks, P.C.

(57) ABSTRACT

The invention relates to a gel composition containing pirfenidone, which is advantageous over other cutaneously administered pharmaceutical forms known in the prior art and which can be used in treatment for the restoration of tissues with fibrotic lesions and for the prevention of fibrotic lesions.

7 Claims, No Drawings

(56) References Cited

U.S. PATENT DOCUMENTS

| | | | |
|---|---|---|---|
| 2005/0059626 | A1 | 3/2005 | Van Nest et al. |
| 2005/0267018 | A1 | 12/2005 | Blatt et al. |
| 2006/0039931 | A1 | 2/2006 | Scheiwe et al. |
| 2006/0051339 | A1 | 3/2006 | Sivak |
| 2006/0115503 | A1 | 6/2006 | Goyal |
| 2006/0198823 | A1 | 9/2006 | Blatt |
| 2007/0054842 | A1 | 3/2007 | Blatt et al. |
| 2007/0117841 | A1 | 5/2007 | Ozes et al. |
| 2007/0128258 | A1 | 6/2007 | Faure et al. |
| 2007/0258946 | A1 | 11/2007 | Blatt |
| 2008/0025986 | A1 | 1/2008 | Ozes et al. |
| 2008/0319026 | A1 | 12/2008 | Gant et al. |
| 2009/0047246 | A1 | 2/2009 | Beigelman et al. |
| 2009/0137354 | A1 | 5/2009 | Chaudhuri |
| 2010/0221217 | A1 | 9/2010 | Porter et al. |
| 2010/0256031 | A1 | 10/2010 | Wu et al. |
| 2011/0034495 | A1 | 2/2011 | Seiwert et al. |
| 2011/0224265 | A1 | 9/2011 | Magana Castro et al. |
| 2011/0288134 | A1 | 11/2011 | Maksumova et al. |
| 2012/0192861 | A1 | 8/2012 | Surber et al. |
| 2012/0283328 | A1 | 11/2012 | Modi |
| 2013/0225639 | A1 | 8/2013 | Robinson et al. |
| 2013/0245073 | A1 | 9/2013 | Magana Castro et al. |
| 2013/0345165 | A1 | 12/2013 | Smith et al. |
| 2014/0296300 | A1 | 10/2014 | Armendariz Borunda et al. |
| 2015/0148382 | A1 | 5/2015 | Armendariz Borunda et al. |
| 2015/0196543 | A1 | 7/2015 | Surber |
| 2015/0231098 | A1 | 8/2015 | Magana Castro et al. |
| 2016/0228424 | A1 | 8/2016 | Armendariz Borunda et al. |
| 2016/0287567 | A1 | 10/2016 | Armendariz Borunda et al. |
| 2016/0338973 | A1 | 11/2016 | Sonti et al. |
| 2016/0338997 | A1 | 11/2016 | Ryan |
| 2017/0216197 | A1 | 8/2017 | McHale et al. |
| 2017/0216268 | A1 | 8/2017 | Magana Castro et al. |
| 2017/0231937 | A1 | 8/2017 | Bolsoy |
| 2018/0066228 | A1 | 3/2018 | Smith et al. |
| 2018/0092893 | A1 | 4/2018 | Armendariz Borunda et al. |
| 2018/0214434 | A1 | 8/2018 | Armendariz Borunda et al. |
| 2018/0353448 | A1 | 12/2018 | Magana Castro et al. |
| 2019/0030012 | A1 | 1/2019 | Surber |
| 2019/0160048 | A1 | 5/2019 | Biber et al. |
| 2019/0262325 | A1 | 8/2019 | Armendariz Borunda et al. |
| 2019/0290606 | A1 | 9/2019 | Magana Castro et al. |
| 2019/0358213 | A1 | 11/2019 | Armendariz Borunda et al. |
| 2020/0016138 | A1 | 1/2020 | Magana Castro et al. |
| 2020/0038386 | A1 | 2/2020 | Armendariz Borunda et al. |
| 2020/0061040 | A1 | 2/2020 | Armendariz Borunda et al. |
| 2020/0253944 | A1 | 8/2020 | Magana Castro et al. |
| 2021/0093593 | A1 | 4/2021 | Magana Castro et al. |
| 2021/0346360 | A1 | 11/2021 | Armendariz Borunda et al. |
| 2021/0386724 | A1 | 12/2021 | Armendariz Borunda et al. |
| 2021/0401989 | A1 | 12/2021 | Armendariz Borunda et al. |
| 2022/0016096 | A1 | 1/2022 | Magana Castro et al. |
| 2023/0117397 | A1 | 4/2023 | Aguilar-Cordova et al. |
| 2023/0165819 | A1 | 6/2023 | Magaña Castro et al. |
| 2023/0181550 | A1 | 6/2023 | Armendáriz Borunda et al. |
| 2024/0216350 | A1 | 7/2024 | Armendariz Borunda et al. |
| 2025/0213539 | A1 | 7/2025 | Armendariz Borunda et al. |
| 2025/0221949 | A1 | 7/2025 | Magana Castro et al. |
| 2025/0325530 | A1 | 10/2025 | Armendariz Borunda et al. |
| 2025/0367177 | A1 | 12/2025 | Armendariz Borunda et al. |

FOREIGN PATENT DOCUMENTS

| | | | |
|---|---|---|---|
| CN | 101972225 | A | 2/2011 |
| CN | 101972236 | A | 2/2011 |
| CN | 102488660 | A | 6/2012 |
| CN | 102670600 | A | 9/2012 |
| CN | 102670632 | A | 9/2012 |
| CN | 103550242 | A | 2/2014 |
| EP | 1113798 | A1 | 7/2001 |
| EP | 1356816 | A1 | 10/2003 |
| EP | 2177220 | A1 | 4/2010 |
| EP | 2832354 | A1 | 2/2015 |
| EP | 2907506 | A1 | 8/2015 |
| ES | 2377932 | T3 | 4/2012 |
| ES | 2530049 | T3 | 2/2015 |
| JP | 8-510251 | A | 10/1996 |
| JP | 2002-506820 | A | 3/2002 |
| JP | 2006-503026 | A | 1/2006 |
| JP | 2011-506446 | A | 3/2011 |
| JP | 2014-505733 | A | 3/2014 |
| JP | 2014-522861 | A | 9/2014 |
| JP | 2015-513359 | A | 5/2015 |
| JP | 2015-526528 | A | 9/2015 |
| JP | 2016-515525 | A | 5/2016 |
| JP | 2016-517444 | A | 6/2016 |
| KR | 10-2014-0057248 | A | 5/2014 |
| KR | 10-2014-0146144 | A | 12/2014 |
| KR | 10-2017-0074497 | A | 6/2017 |
| MX | 2013008151 | A | 10/2013 |
| WO | WO 97/10712 | A1 | 3/1997 |
| WO | WO 99/047140 | A1 | 9/1999 |
| WO | WO 2000/16775 | A1 | 3/2000 |
| WO | WO 2004/073713 | A1 | 9/2004 |
| WO | WO 2004/078193 | A1 | 9/2004 |
| WO | WO 2004/078194 | A1 | 9/2004 |
| WO | WO 2004/078207 | A1 | 9/2004 |
| WO | WO 2004/089283 | A2 | 10/2004 |
| WO | WO 2005/000227 | A2 | 1/2005 |
| WO | WO 2005/013917 | A2 | 2/2005 |
| WO | WO 2005/037214 | A2 | 4/2005 |
| WO | WO 2006/122154 | A2 | 11/2006 |
| WO | WO 2007/038315 | A2 | 4/2007 |
| WO | WO 2008/107873 | A1 | 9/2008 |
| WO | WO 2009/022899 | A1 | 2/2009 |
| WO | WO 2010/054294 | A1 | 5/2010 |
| WO | WO 2010/132864 | A1 | 11/2010 |
| WO | WO 2012/106382 | A1 | 8/2012 |
| WO | WO 2013/012307 | A1 | 1/2013 |
| WO | WO 2013/147577 | A1 | 10/2013 |
| WO | WO 2013/181691 | A1 | 12/2013 |
| WO | WO 2014/036487 | A1 | 3/2014 |
| WO | WO 2014/055548 | A1 | 4/2014 |
| WO | WO 2016/185182 | A1 | 11/2016 |
| WO | WO 2017/104725 | A1 | 6/2017 |
| WO | WO 2018/088886 | A1 | 5/2018 |
| WO | WO 2018/189012 | A1 | 10/2018 |
| WO | WO 2019/035705 | A2 | 2/2019 |
| WO | WO 2020/227331 | A1 | 11/2020 |

OTHER PUBLICATIONS

International Preliminary Report on Patentability, dated Jan. 28, 2019 for Application No. PCT/MX2017/000129.

International Search Report and Written Opinion, dated Jun. 5, 2013 for Application No. PCT/MX2013/000027.

International Preliminary Report on Patentability dated Oct. 9, 2014 for Application No. PCT/MX2013/000027.

International Search Report and Written Opinion, dated Aug. 8, 2014 for Application No. PCT/MX2013/000099.

International Preliminary Report on Patentability, dated Dec. 19, 2014 for Application No. PCT/MX2013/000099.

International Search Report and Written Opinion, dated Mar. 28, 2019 for Application No. PCT/MX2018/000071.

International Preliminary Report on Patentability, dated Jul. 19, 2019 for Application No. PCT/MX2018/000071.

International Search Report and Written Opinion, dated Jul. 12, 2021 for Application No. PCT/US2021/027335.

International Preliminary Report on Patentability, dated Oct. 27, 2022 for Application No. PCT/US2021/027335.

International Search Report and Written Opinion, dated Aug. 4, 2020 for Application No. PCT/MX2019/000093.

International Preliminary Report on Patentability, dated Jan. 12, 2021 for Application No. PCT/MX2019/000093.

[No Author Listed], Allicinnow, "allicin," retrieved online at: http://www.allicinnow.com/allicin/acne-treatmentl, 2 pages (2010).

[No Author Listed], Application of addition polymers in hydrophilic hydroxypropyl methylcellulose extended release matrix tablets. Colorcon China, Inc. China Academic Journal Electronic Publishing House. 2022. 3 pages.

(56) References Cited

OTHER PUBLICATIONS

[No Author Listed], Efficacy of Pirfenidone Plus MODD in diabetic foot ulcers. NCT02632877. Last updated: Dec. 17, 2015. Retrieved May 17, 2022 from <https://clinicaltrials.gov/ct2/show/NCT02632877?term=NCT02632877>. 8 pages.
[No Author Listed], Mexico's coronavirus death toll is likely 60% higher than confirmed numbers. Reuters. Mar. 29, 2021. Accessed from <https://www.nbcnews.com/news/latino/mexicos-coronavirus-death-toll-likely-60-higher-confirmed-numbers-rcna531> on Jan. 10, 2023. 3 pages.
[No Author Listed], Severe Outcomes Among Patients with Coronavirus Disease 2019 (COVID-19)—United States, Feb. 12-Mar. 16, 2020. CDC COVID-19 Response Team. MMWR Morb Mortal Wkly Rep. Mar. 27, 2020;69(12):343-346. doi: 10.15585/mmwr.mm6912e2.
[No Author Listed], Understanding Acne Treatment. Retrieved from <https:/www.webmd.com/skin-problems-and-treatments/acne/understanding-acne-treatment#5> on Feb. 4, 2019. 5 pages.
Armendariz-Borunda et al., A controlled clinical trial with pirfenidone in the treatment of pathological skin scarring caused by burns in pediatric patients. Ann Plast Surg. Jan. 2012;68(1):22-8. doi: 10.1097/SAP.0b013e31821b6d08.
Armendáriz-Borunda et al., A pilot study in patients with established advanced liver fibrosis using pirfenidone. Gut. Nov. 2006;55(11):1663-5. doi: 10.1136/gut.2006.107136.
Azuma et al., Double-blind, placebo-controlled trial of pirfenidone in patients with idiopathic pulmonary fibrosis. Am J Respir Crit Care Med. May 1, 2005;171(9):1040-7. doi: 10.1164/rccm.200404-571OC. Epub Jan. 21, 2005.
Bednarek et al., Skin Antiseptics. In:StatPearls. Jan. 2022. Retrieved from https://www.ncbi.nlm.nih.gov/books/NBK507853 Jun. 9, 2022.
Bhatraju et al., Covid-19 in Critically Ill Patients in the Seattle Region—Case Series. N Engl J Med. May 21, 2020;382(21):2012-2022. doi: 10.1056/NEJMoa2004500. Epub Mar. 30, 2020.
Bruss et al., Pharmacokinetics of orally administered pirfenidone in male and female beagles. J Vet Pharmacol Ther. Oct. 2004;27(5):361-7. doi: 10.1111/j.1365-2885.2004.00612.x.
Cain et al., Inhibition of tumor necrosis factor and subsequent endotoxin shock by pirfenidone. Int J Immunopharmacol. Dec. 1998;20(12):685-95. doi: 10.1016/s0192-0561(98)00042-3.
Chen et al., Early detection of nonalcoholic steatohepatitis in patients with nonalcoholic fatty liver disease by using MR elastography. Radiology. Jun. 2011;259(3):749-56. doi: 10.1148/radiol.11101942. Epub Apr. 1, 2011.
Choudhuri et al., SARS-CoV-2 PCR cycle threshold at hospital admission associated with patient mortality. PLoS One. Dec. 31, 2020;15(12):e0244777. doi: 10.1371/journal.pone.0244777.
Database WPI Section Ch, Week 200629 Thomson Scientific, London, GB; Class B03, AN 2006-273778, Wu, Use of pirfenidone for treating hepatic injury and necrosis and acute lung injury. Shanghai Genomics. p. 7; (2005).
Database WPI Section Ch, Week 201139 Thomson Scientific, London, GB; Class A96, AN 2011-D92901, Li X: Sustained-release tablet comprises pirfenidone, substance capable of releasing active ingredient, and additive, Med; Pharm Sci& Technology Co , 1 page (2011).
Database WPI Section Ch, Week 201427 Thomson Scientific, London, GB; Class A96, AN 2014-F77081, Deng C et al., Pharmaceutical composition used for treating hepatic fibrosis, liver fibrosis, liver cirrhosis, and liver cancer comprises pirfenidone, inosine, and auxiliary materials. Sichuan Guokang Pharm Co Ltd, 1 page (2014).
Didiasova et al., Pirfenidone exerts antifibrotic effects through inhibition of GLI transcription factors. FASEB J. May 2017;31(5):1916-1928. doi: 10.1096/fj.201600892RR. Epub Feb. 1, 2017.
Gancedo et al., Pirfenidone prevents capsular contracture after mammary implantation. Aesthetic Plast Surg. Jan. 2008;32(1):32-40. doi: 10.1007/s00266-007-9051-4.
Gao et al., Pirfenidone Alleviates Choroidal Neovascular Fibrosis through TGF-β/Smad Signaling Pathway. J Ophthalmol. Feb. 10, 2021;2021:8846708. doi: 10.1155/2021/8846708.
Garcia et al., Pirfenidone effectively reverses experimental liver fibrosis. J Hepatol. Dec. 2002;37(6):797-805.
Gennaro, Remington's Pharmaceutical Sciences. 1990; 18th Ed. pp. 1288-1289, 1291-1292.
Gu et al., Pirfenidone inhibits cryoablation induced local macrophage infiltration along with its associated TGFb1 expression and serum cytokine level in a mouse model. Cryobiology. Jun. 2018;82:106-111. doi: 10.1016/j.cryobiol.2018.03.012. Epub Apr. 3, 2018.
Guo et al., Pirfenidone inhibits epithelial-mesenchymal transition and pulmonary fibrosis in the rat silicosis model. Toxicol Lett. Jan. 2019;300:59-66. doi: 10.1016/j.toxlet.2018.10.019. Epub Oct. 28, 2018.
Güvenç et al., Pirfenidone Attenue Epidural Fibrosis In Rats By Suppressing TNF-α, IL-1, and α-SMA. J Turk Spin Surg. Jul. 2018;29(3):133-40.
Huang et al., Clinical features of patients infected with 2019 novel coronavirus in Wuhan, China. Lancet. Feb. 15, 2020;395(10223):497-506. doi: 10.1016/S0140-6736(20)30183-5. Epub Jan. 24, 2020. Erratum in: Lancet. Jan. 30, 2020.
Ishinaga et al., TGF-β induces p65 acetylation to enhance bacteria-induced NF-κB activation. EMBO J. Feb. 21, 2007;26(4):1150-62. doi: 10.1038/sj.emboj.7601546. Epub Feb. 1, 2007.
Janka-Zires et al., Topical Administration of Pirfenidone Increases Healing of Chronic Diabetic Foot Ulcers: A Randomized Crossover Study. J Diabetes Res. 2016;2016:7340641. doi: 10.1155/2016/7340641. Epub Jul. 10, 2016.
Josling, Peter Josling's PowerPoint on AllicinCenter Products and Their Uses. retrieved from the internet at: http://allicincenter.com/reference.php?id=products, 15 pages (2013).
King et al., A phase 3 trial of pirfenidone in patients with idiopathic pulmonary fibrosis. N Engl J Med. May 29, 2014;370(22):2083-92. doi: 10.1056/NEJMoa1402582. Epub May 18, 2014. Erratum in: N Engl J Med. Sep. 18, 2014;371(12):1172.
Loomba et al., GS-0976 Reduces Hepatic Steatosis and Fibrosis Markers in Patients With Nonalcoholic Fatty Liver Disease. Gastroenterology. Nov. 2018;155(5):1463-1473.e6. doi: 10.1053/j.gastro.2018.07.027. Epub Jul. 27, 2018.
Lopez-De La Mora et al., Role and New Insights of Pirfenidone in Fibrotic Diseases. Int J Med Sci. Oct. 14, 2015;12(11):840-7. doi: 10.7150/ijms.11579.
Macias-Barragan et al., Methyl-1-Phenyl-2-(1H)-Pyridone Treatment Improves Markers of Hepatic Function and Fibrosis in Steatosis Included By High Fat/Carbohydrate Diet. J Hepatology, Abstract of the International Liver Congress™ 2014—49th Annual Meeting of the European Association for the Study of the Liver, Abstract P428, 'ol. 60(1)Suppl.1: S210 (2014).
Macias-Barragan et al., Pirfenidone LP activates PPARalpha and LXRalpha and results in decreased expression of proinflammatory cytokines and improvement of NASH features induced by high fat/carbohydrate diet. Hepatology—Special Issue: The 67th Annual Meeting of the American Association for the Study of Liver Diseases: The Liver Meeting 2016, Abstract No. 1541: vol. 64(SI): 767A-768A: 2 pages (2016).
Mccommis et al., Treating Hepatic Steatosis and Fibrosis by Modulating Mitochondrial Pyruvate Metabolism. Cell Mol Gastroenterol Hepatol. 2019;7(2):275-284. doi: 10.1016/j.jcmgh.2018.09.017. Epub Oct. 10, 2018.
Moises et al., A Double-blind, Multicenter Study Comparing Pirfenidone and Prednisone for Moderate-to-Severe Pulmonary Fibrosi. Chest J. Jan. 1, 2003;124(4)Suppl:116S. Abstract Only. doi: 10.1378/chest.124.4_MeetingAbstracts.116S-b.
Nagai et al., Open-label compassionate use one year-treatment with pirfenidone to patients with chronic pulmonary fibrosis. Intern Med. Dec. 2002;41(12):1118-23. doi: 10.2169/internalmedicine.41.1118.
Nakanishi et al., Pirfenidone inhibits the induction of iNOS stimulated by interleukin-lbeta at a step of NF-kappaE DNA binding in hepatocytes. J Hepatology, vol. 41(5):730-736 (2004).

(56) References Cited

OTHER PUBLICATIONS

Nakazato et al., A novel anti-fibrotic agent pirfenidone suppresses tumor necrosis factor-alpha at the translational level. Eur J Pharmacol. Jun. 20, 2002;446(1-3):177-85. doi: 10.1016/s0014-2999(02)01758-2.
Ojeda-Duran et al., Evaluation of Safety of a Newly Formulated Pirfenidone in Chronic Kidney Disease: A Non-Randomized Pilot Study in Mexican Patients. J Renal Hepatic Disorders. 2020;4(1):22-30.
Oku et al., Pirfenidone suppresses tumor necrosis factor-alpha, enhances interleukin-10 and protects mice from endotoxic shock. Eur J Pharmacol. Jun. 20, 2002;446(1-3):167-76. doi: 10.1016/s0014-2999(02)01757-0.
Olivas-Martinez et al., In-hospital mortality from severe COVID-19 in a tertiary care center in Mexico City; causes of death, risk factors and the impact of hospital saturation. PLoS One. Feb. 3, 2021;16(2):e0245772. doi: 10.1371/journal.pone.0245772. Erratum in: PLoS One. May 23, 2022;17(5):e0269053.
Orozco et al., Economic evaluation of topical administration of gel with pirfenidone (Kitoscell Q®) as an adjuvant in the treatment of patients with diabetic foot ulcers. PMD63. Value in Health. May 2017; 20(5):A246.
Ozes et al., Preclinical activity of pirfenidone (5-methyl-lphenyl-2 (IH)-pyri done) in cell-based models of nonalcoholic steatohepatitis. Hepatology, Abstract 697, 2003;34(4): 495A.
Park et al., Pirfenidone suppressed the development of glomerulosclerosis in the FGS/Kist mouse. J Korean Med Sci. Aug. 2003;18(4):527-33.
Pepin, K., Liver Fat Does Not Affect Liver Stiffness Measured with MR Elastography. Resoundant Fact Sheet. 2019. Accessed from < https://www.resoundant.com/single-post/2019/05/21/fact-sheet-liver-fat-does-not-affect-liver-stiffness-measured-with-mr-elastography> on Sep. 21, 2022. 2 pages.
Raghu et al., Treatment of idiopathic pulmonary fibrosis with a new antifibrotic agent, pirfenidone: results of a prospective, open-label Phase II study. Am J Respir Crit Care Med. Apr. 1999;159(4 Pt 1):1061-9. doi: 10.1164/ajrccm.159.4.9805017.
Rao et al., A Systematic Review of the Clinical Utility of Cycle Threshold Values in the Context of COVID-19. Infect Dis Ther. Sep. 2020;9(3):573-586. doi: 10.1007/s40121-020-00324-3. Epub Jul. 28, 2020. Erratum in: Infect Dis Ther. Aug. 18, 2020.
Ravishankar et al., A brief review on Pleiotropic effects of Pirfenidone—novel and ongoing outcomes. Int J Res Dev Pharm Life Sci. Jan.-Feb. 2019;8(1):6-14. doi: 10.21276/IJRDPL.2278-0238.2019.8(1).6-14.
Rubino et al., Effect of food and antacids on the pharmacokinetics of pirfenidone in older healthy adults. Pulm Pharmacol Ther. Aug. 2009;22(4):279-85. doi: 10.1016/j.pupt.2009.03.003. Epub Mar. 27, 2009.
Ruwanpura et al., Pirfenidone: Molecular Mechanisms and Potential Clinical Applications in Lung Disease. Am J Respir Cell Mol Biol. Apr. 2020;62(4):413-422. doi: 10.1165/rcmb.2019-0328TR.
Salazar-Montes et al., Potent antioxidant role of pirfenidone in experimental cirrhosis. Eur J Pharmacol. Oct. 24, 2008;595(1-3):69-77. doi: 10.1016/j.ejphar.2008.06.110. Epub Jul. 9, 2008.
Schaefer et al., Antifibrotic activities of pirfenidone in animal models. Eur Respir Rev. Jun. 2011;20(120):85-97. doi: 10.1183/09059180.00001111.
Selman et al., Idiopathic pulmonary fibrosis: prevailing and evolving hypotheses about its pathogenesis and implications for therapy. Ann Intern Med. Jan. 16, 2001;134(2):136-51. doi: 10.7326/0003-4819-134-2-200101160-00015.
Selvaraj et al., Diagnostic accuracy of elastography and magnetic resonance imaging in patients with NAFLD: A systematic review and meta-analysis. J Hepatol. Oct. 2021;75(4):770-785. doi: 10.1016/j.jhep.2021.04.044. Epub May 13, 2021.
Suga et al., Preventive effect of pirfenidone against experimental sclerosing peritonitis in rats. Exp Toxicol Pathol. Sep. 1995;47(4):287-91. doi: 10.1016/s0940-2993(11)80261-7.
Sun et al., Pharmacokinetic and pharmacometabolomic study of pirfenidone in normal mouse tissues using high mass resolution MALDI-FTICR-mass spectrometry imaging. Histochem Cell Biol. Feb. 2016;145(2):201-11. doi: 10.1007/s00418-015-1382-7. Epub Dec. 8, 2015.
Sun et al., Pharmacometabolic response to pirfenidone in pulmonary fibrosis detected by MALDI-FTICR-MSI. Eur Respir J. Sep. 15, 2018;52(3):1702314. doi: 10.1183/13993003.02314-2017.
Tiwari et al., Applications of Complementary Polymers in HPMC Hydrophilic Extended Release Matrices. Drug Delivery Technology, Formulating Hydrophilic Matrix Systems, 2009;9(7), 7 pages.
Veras-Castillo et al., Controlled clinical trial with pirfenidone in the treatment of breast capsular contracture: Association of TGF polymorphisms. Annals Plastic Surgery. 2014;70(1):16-22.
Wang et al., Clinical Features of 69 Cases With Coronavirus Disease 2019 in Wuhan, China. Clin Infect Dis. Jul. 28, 2020;71(15):769-777. doi: 10.1093/cid/ciaa272.
Wang et al., Remdesivir and chloroquine effectively inhibit the recently emerged novel coronavirus (2019-nCoV) in vitro. Cell Res. Mar. 2020;30(3):269-271. doi: 10.1038/s41422-020-0282-0. Epub Feb. 4, 2020.
Wilson et al., Another Weapon in the Battle against Idiopathic Pulmonary Fibrosis? Am J Respir Cell Mol Biol. Apr. 2019;60(4):386-387. doi: 10.1165/rcmb.2018-0387ED.
Wu et al., Risk Factors Associated With Acute Respiratory Distress Syndrome and Death in Patients With Coronavirus Disease 2019 Pneumonia in Wuhan, China. JAMA Intern Med. Jul. 1, 2020;180(7):934-943. doi: 10.1001/jamainternmed.2020.0994. Erratum in: JAMA Intern Med. Jul. 1, 2020;180(7):1031.
Wygrecka et al., Pirfenidone exerts anti-fibrotic effects through Inhibition of GLI transcription factors. Pneumologie. Feb. 21, 2018;72(S 01):S114-5. doi: 10.1055/s-0037-1619431.
Zhang et al., Liver fibrosis imaging: A clinical review of ultrasound and magnetic resonance elastography. J Magn Reson Imaging. Jan. 2020;51(1):25-42. doi: 10.1002/jmri.26716. Epub Mar. 12, 2019. Author Manuscript, 32 pages.
Zhang et al., Pirfenidone reduces fibronectin synthesis by cultured human retinal pigment epithelial cells. Aust N Z J Ophthalmol. May 1998;26 Suppl 1:S74-6. doi: 10.1111/j.1442-9071.1998.tb01380.x.
Zhou et al., Clinical course and risk factors for mortality of adult inpatients with COVID-19 in Wuhan, China: a retrospective cohort study. Lancet. Mar. 28, 2020;395(10229):1054-1062. doi: 10.1016/S0140-6736(20)30566-3. Epub Mar. 11, 2020. Erratum in: Lancet. Mar. 28, 2020;395(10229):1038. Erratum in: Lancet. Mar. 28, 2020;395(10229):1038.
Ziol et al., Noninvasive assessment of liver fibrosis by measurement of stiffness in patients with chronic hepatitis C. Hepatology. Jan. 2005;41(1):48-54. doi: 10.1002/hep.20506.
Partial Supplementary European Search Report, dated Apr. 16, 2024 for EP Application No. 21788910.4.
Extended European Search Report, dated Jul. 12, 2024 for EP Application No. 21788910.4.
[No Author Listed], A randomized, open-label study to evaluate the efficacy and safety of Pirfenidone in patients with severe and critical novel coronavirus infection (COVID-19). World Health Organization International Clinical Trials Registry. Feb. 28, 2020. Accessed from <https://trialsearch.who.int/Trial2.aspx?TrialID=ChiCTR2000030333>. 3 pages.
[No Author Listed], Efficacy and Safety of Pirfenidone in the Treatment of Severe Post-Novel Coronavirus Pneumonia (COVID-19)) Fibrosis: a prospective exploratory experimental medical study. World Health Organization International Clinical Trials Registry. Mar. 6, 2020. Accessed from <https://trialsearch.who.int/Trial2.aspx?TrialID=ChiCTR2000030892>. 2 pages.
[No Author Listed], History of Changes for Study: NCT04282902; A Study to Evaluate the Efficacy and Safety of Pirfenidone With Novel Coronavirus Infection. Feb. 21, 2020. Accessed from <https://classic.clinicaltrials.gov/ct2/history/NCT04282902?V_1=View#StudyPageTop>. 10 pages.
Dai et al., High-resolution Chest CT Features and Clinical Characteristics of Patients Infected with COVID-19 in Jiangsu, China. Int J Infect Dis. Jun. 2020;95:106-112. doi: 10.1016/j.ijid.2020.04.003. Epub Apr. 6, 2020.

(56) References Cited

OTHER PUBLICATIONS

Estes et al., Antifibrotic therapy in simian immunodeficiency virus infection preserves CD4+ T-cell populations and improves immune reconstitution with antiretroviral therapy. J Infect Dis. Mar. 1, 2015;211(5):744-54. doi: 10.1093/infdis/jiu519. Epub Sep. 22, 2014.
Flores-Contreras et al., Treatment with pirfenidone for two years decreases fibrosis, cytokine levels and enhances CB2 gene expression in patients with chronic hepatitis C. BMC Gastroenterol. Jul. 27, 2014;14:131. doi: 10.1186/1471-230X-14-131.
Horie et al., Emerging pharmacological therapies for ARDS: COVID-19 and beyond. Intensive Care Med. Dec. 2020;46(12):2265-2283. doi: 10.1007/s00134-020-06141-z. Epub Jul. 11, 2020.
Lewis, T., Here's what we know about the most touted drugs tested for COVID-19. Scientific American. Apr. 16, 2020. Accessed May 16, 2025 from <https://www.scientificamerican.com/article/heres-what-we-know-about-the-most-touted-drugs-tested-for-covid-19/>. 10 pages.
Lovelace et al., Dr. Anthony Fauci warns US could 'be in for a bad fall' if coronavirus treatments don't work. CNBC, Health and Science. Apr. 28, 2020. Accessed May 16, 2025 from <https://rb.gy/a2pf8q>. 3 pages.
Seifirad, S., Pirfenidone: A novel hypothetical treatment for COVID-19. Med Hypotheses. Nov. 2020;144:110005. doi: 10.1016/j.mehy.2020.110005. Epub Jun. 17, 2020.
Vitiello et al., COVID-19 Patients with Pulmonary Fibrotic Tissue: Clinical Pharmacological Rational of Antifibrotic Therapy. SN Compr Clin Med. 2020;2(10):1709-1712. doi: 10.1007/s42399-020-00487-7. Epub Aug. 27, 2020.
Xu et al., Key Points of Clinical and CT Imaging Features of 2019 Novel Coronavirus (2019-nCOV) Imported Pneumonia Based On 21 Cases Analysis. medRxiv. Mar. 6, 2020. doi: 10.1101/2020.03.03.20030775. 14 pages.

GEL CONTAINING PIRFENIDONE

RELATED APPLICATIONS

This application is continuation of and claims priority under 35 U.S.C. § 120 to U.S. patent application U.S. Ser. No. 17/390,368, filed Jul. 30, 2021, which is a continuation of and claims priority under 35 U.S.C. § 120 to U.S. patent application Ser. No. 16/450,150, filed Jun. 24, 2019, which is a divisional application of and claims priority under 35 U.S.C. § 120 to U.S. patent application Ser. No. 15/435,494, filed on Feb. 17, 2017, which is a divisional application of and claims priority under 35 U.S.C. § 120 to U.S. patent application, U.S. Ser. No. 13/893,626, filed on May 14, 2013, which is a divisional application of and claims priority under 35 U.S.C. § 120 to U.S. patent application Ser. No. 12/673,304, filed on Apr. 28, 2010, which is a national stage filing under 35 U.S.C. § 371 of International Application PCT/MX2008/000107, filed on Aug. 14, 2008, which claims priority to Mexican Patent Application Serial No. MX/a/2007/009796, filed on Aug. 14, 2007, each of which is hereby-incorporated herein by reference.

FIELD OF INVENTION

The present invention is related to a gel formula that contains Pirfenidone, which offers advantages over other pharmaceutical forms of known cutaneous administration in the state of the technique.

BACKGROUND OF THE INVENTION

The 5-methyl-1-phenyl-2(1H)-pyridone, formula;

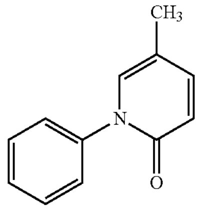

It is a drug that has been applied in the restoration of tissues with lesions with fibrosis and the prevention of fibrotic lesions. This compound, Pirfenidone, it is by itself a known compound and its pharmacological effects has been described, for example, in Japanese applications numbers 87677/1974 and 1284338/1976, as an anti-inflammatory agent that includes antipyretic and analgesics. The U.S. Pat. No. 3,839,346, published Oct. 1, 1974; the U.S. Pat. No. 3,974,281, published Aug. 10, 1976; the U.S. Pat. No. 4,042,699 published Aug. 16, 1977, and the U.S. Pat. No. 4,052,509 published Oct. 4, 1977, which described the methods for the obtained Pirfenidone, as well as its use as an anti-inflammatory agent. In the Mexican patent 182, 266 the antifibrotic activity of the 5-methyl-1-phenyl-2(1H)-pyridone is described.

Different resources and treatments have been used to the date and none of them have shown to be really effective. Pirfenidone has shown its efficacy as an anti-fibrotic agent in different pathologies and organs, and has been demonstrated in previous works, where we have observed an effect on the fibroblasts and the production of collagen and extracellular matrix, as well as in experimental models and in clinical tests also.

Many substances could form gels when a gelificant agent is added. This is use in many diverse products in the manufacturing industry, from food to paint, passing through adhesives.

Gels are also important in the chemistry part related with the processes SOL_GEL and in the synthesis of solid materials with nanopores.

Gels are classified in: aqueous (hydrogels) or organic (organogels), depending if the aqueous component is water or an organic solvent; organic or inorganic in nature, colloidal or thick grain, according to the size of the particles; and rigid gels, elastic or tixothrophic, according to its mechanic properties.

The hydrocolloids are substances that are produced from vegetable and animal proteins or multiple sugars. They have the capacity to swell themselves and to bind to water. The hydrocolloids are used to thicken, solidify and stabilize food.

OBJECT OF THE INVENTION

The object of the present invention is to provide a gel composition for its cutaneous administration that contains Pirfenidone, a viscous agent; a solubilizer; a non ionic solubilizer; a conserving agent; a neutralizer agent and purified water.

Also, it is the object of the present invention to provide a process of manufacture of a gel that contains pirfenidone for its cutaneous application.

Another objective of the present invention is to provide a gel medicine to be used as an anti-fibrotic and anti-inflammatory agent.

SPECIFICATION OF THE INVENTION

Composition of the Gel

The composition of the gel contains from 2 to 12% of Pirfenidone is elaborated utilizing from 0.4 to 1.2% of a viscous agent, from 10 to 30% of a solubilizer, from 5 to 15% of a non ionic solubilizer, from 0.2 to 1% of a conserving agent, from 0.4 to 1.2% a neutralizer agent and the rest of purify water. The viscous agent is selected from a carbomer 940 (MR); Ultrex 10(MR), cellulose derivatives; gums; polioxameres; ethylic alcohol and propylenglycol; the conserving agent is selected from a group that consist of Diazolidinyl urea, iodopropinil-butilcarbamate; methylparabene and a mix of these compounds; the neutralizer agent is selected from a group of primary, secondary and tertiary aliphatic amines of the mono-, bi- and triethanolamine type, and of the hydroxide alkaline metals, such as sodium hydroxide.

An example of the composition of the gel is shown in the table 1:

| Component | Quantity (g) | % |
|---|---|---|
| Pirfenidone | 8 | 8 |
| Viscous agent | 0.5 | 0.5 |
| Solubilizer | 20 | 20 |
| Non ionic solubilizer | 11.5 | 11.5 |
| Conserving agent | 0.5 | 0.5 |
| Neutralizer | 0.5 | 0.5 |
| Purified water up to | 100 | 59 |

The gel containing Pirfenidone is manufactured as follows:

a) Mix 50% of the total water to be used with the viscous agent, allowing the complete humectation of the viscous agent;

b) Mix separately and with constant agitation the Pirfenidone with the solubilizer agent;

c) Dissolve separately the non ionic solubilizer agent in the 25% water to be used at 40° C., once dissolved, the 15% of the total water is added;

d) Add the solution from part c) to the mix from part b), agitate until the mix is homogenate.

e) Dilute the neutralizer agent in 10% of the total water to use, agitate until the mix is homogenate; and f) Add with constant agitation and homogenate in each addition to the mix from part a) the solution from part d); the conservative and the solution from part e).

A prepared composition according to procedure describe is shown in table 2.

| Component | Quantity (g) |
|---|---|
| Pirfenidone | 8 |
| Carbomer | 0.5 |
| N-methylpirrolidone | 20 |
| Macrogolglycerol Hidroxiestearate 40 | 11.5 |
| Diazolidinilurea and Iodopropinil-butilcarbamate | 0.5 |
| Triethanoalamine | 0.5 |
| Purified water up to | 100 |

These compositions are shown in an example mode, but they are not limited in any level of the reach of the description of the present invention.

The invention claimed is:

1. A composition of pirfenidone gel consisting of:

(i) 2-12% pirfenidone;

(ii) 0.4-1.2% of Carbomer 940®;

(iii) 10-30% of N-methylpyrrolidone;

(iv) 5-15% of macrogolglycerol hydroxystearate 40;

(v) 0.2-1% of diazolidinyl urea and iodopropynyl butylcarbamate;

(vi) 0.4-1.2% of triethanolamine; and (vii) water.

2. The composition of claim 1, wherein the composition consists of 8% pirfenidone, 0.5% of Carbomer 940®, 20% of N-methylpyrrolidone, 11.5% of macrogolglycerol hydroxystearate 40, 0.5% of diazolidinyl urea and iodopropynyl butylcarbamate, 0.5% of triethanolamine, and 59% of water.

3. The composition of claim 1, wherein the composition is an anti-fibrotic composition.

4. The composition of claim 1, wherein the composition is an anti-inflammatory composition.

5. The composition of claim 1, wherein the composition consists of:

(i) 8% pirfenidone;

(ii) 0.5% of Carbomer 940®;

(iii) 10-30% of N-methylpyrrolidone;

(iv) 5-15% of macrogolglycerol hydroxystearate 40;

(v) 0.5% of diazolidinyl urea and iodopropynyl butylcarbamate;

(vi) 0.5% of triethanolamine; and (vii) water.

6. The composition of claim 5, wherein the composition is an anti-fibrotic composition.

7. The composition of claim 5, wherein the composition is an anti-inflammatory composition.

* * * * *